United States Patent [19]

Tran-Cong et al.

[11] Patent Number: 4,772,745

[45] Date of Patent: Sep. 20, 1988

[54] POLYMER-REACTIVE PHOTOSENSITIVE ANTHRACENES

[75] Inventors: Qui Tran-Cong, Germantown; Charles C. Han, Rockville, both of Md.

[73] Assignee: The United States of America as represented by the Secretary of Commerce, Washington, D.C.

[21] Appl. No.: 897,227

[22] Filed: Aug. 18, 1986

[51] Int. Cl.[4] .............................................. C07C 69/34
[52] U.S. Cl. .................................... 560/146; 568/659
[58] Field of Search ......................... 560/146; 568/659

[56] References Cited

PUBLICATIONS

Chemical Abstract, 91:174444, "Study of Nonconjugated Bichromorphic Systems . . . ", Castellan et al., J. Chem. Soc., 1979.

Chem. Abstract, 3688y, "Reactions of Copper Halides with Organic Compounds . . . ", Mosnaim et al., J. Chem. Soc., 1970.

Primary Examiner—Joseph L. Schofer
Assistant Examiner—Bernard Lipman
Attorney, Agent, or Firm—Thomas Zack; Alvin Englert; Albert Tockman

[57] ABSTRACT

Photosensitive anthracene compounds containing two anthracene rings joined by a flexible linkage, and containing a functional group as an annular substituent on one of the anthracene rings, react with polymers to form materials useful in information proceedings.

4 Claims, No Drawings

POLYMER-REACTIVE PHOTOSENSITIVE ANTHRACENES

BACKGROUND OF THE INVENTION

1. Field of the Invention

This invention relates to novel photosensitive anthracene compounds which are polymer-reactive, i.e., contain annular substituents capable of reacting with polymers.

2. Description of the Prior Art

Optical information storage materials play an important role in a variety of practical applications. One such application is information processing, for example, in recording and reading-out of information. The requirements for these materials include good sensitivity to radiation, non-destructive reading-out properties and erasability for repeatable usage. Furthermore, the materials should be easily handled for various types of mechanical processing.

Polymers functionalized with photosensitive groups called "chromophores" have been used for information processing. On irradiation with light, the photosensitive chromophores undergo photoreactions, giving rise to large changes in certain optical properties. In almost all cases, these changes are variations in absorption spectra and/or refractive indices. Except for some special cases, such as polydiacetylene and polyvinylcarbazole, the polymers themselves do not undergo any changes in physical properties on irradiation with light.

The simplest way to prepare polymeric materials containing photosensitive groups is to dope photosensitive molecules, called dopants, into polymer matrices, and to use the whole system as a recording material. This technique has the advantage of avoiding complicated organic syntheses involving chemical attachment of photosensitive groups to polymer chains, but is limited by the compatibility and chemical affinity of the dopants and the polymer matrices. A low level of compatibility can cause aggregation or crystallization of the dopants in the matrices. Such aggregations not only limits the concentration of dopant in a matrix, but also changes the kinetics of photoreactions of the dopant and the optical properties of the material.

Anthracenes, on irradiation with U.V. light, in solution as well as in the crystalline state, dimerize and give the photoproduct, the so-called photodimer, which has optical properties quite different from those of the corresponding anthracenes monomers. Under appropriate conditions, the photodimerization reaction is reversible. U.S. Pat. Nos. 3,807,999 and 3,892,642 describe compounds where two anthracenes are linked together by a flexible chain, which favors dimer formation.

SUMMARY OF THE INVENTION

In its broadest aspect, the present invention is a photosensitive compound containing two anthracene rings linked together by a flexible chain, characterized by the presence of a polymer-reactive functional group as an annular substituent on one of the anthracene rings. The functional group is capable of reacting with an appropriate polymer and the anthracene moiety is chemically incorporated into that polymer.

On irradiation with near visible U.V. light (365 nm), the linked anthracene moiety undergoes intramolecular photodimerization and give rise to a large change in refractive indices in the visible wavelength regions. And, when polymers bearing these groups are irradiated with short U.V. light (254 nm), dimerization is reversed. Thus, the photoerasability of refractive index change can be achieved.

The compounds of the present invention can be described as having the structure:

$$An-R_1-An-R_2$$

wherein An— represents 9-anthryl, —An— represent 9,10-anthrylidine, $R_1$ represents a flexible chain and $R_2$ is a reactive functional group. More specifically $R_1$ is $CH_2-O-CH_2$, $CH_2-CH_2-CH_2$ or $OOC-CH_2-COO$; and $R_2$ is $CH_2OH$, $CH_2Cl$, $COOH$, $COCl$, $CHO$ or $NCO$.

EMBODIMENTS

The novel compounds of the present invention, depending on the chemical natures of the linking group and of the polymer group, are prepared by a variety of reactions well known to those skilled in the art of organic chemistry. For example, those compounds wherein the linking group is $CH_2-O-CH_2$, are prepared as follows:

$$An-CH_2Cl + HOCH_2-An-CH_2OH \rightarrow An-CH_2OCH_2-An-CH_2OH$$

$$ClCH_2-An-CH_2Cl + HOCH_2-An-H \rightarrow An-CH_2OCH_2-An-CH_2Cl$$

$$An-CH_2OH + ClCH_2-An-COOH \rightarrow An-CH_2OCH_2OCH_2-An-COOH$$

9-choromethylanthracene and 9,10-bis(chloromethyl)anthracene are prepared by the chloromethylation of anthracene with paraformaldehyde and HCl. The monochloromethyl compound and the bis(chloromethyl) compound are converted to the corresponding hydroxy compounds by reaction with sodium or potassium acetate followed by alkaline saponification of the intermediate acetate ester.

Compounds wherein the linkage is $CH_2CH_2CH_2$, are prepared by chloromethylation of 9,9'-dianthrylpropane, conversion of the chloromethyl compound to the corresponding hydroxy compound via the acetate ester using the procedure described above, and oxidation of the hydroxy compound to the corresponding carboxylic acid, as shown in the equations which follow:

$$An-CH_2CH_2CH_2-An \rightarrow An-CH_2CH_2CH_2-An-CH_2Cl$$

$$An-CH_2CH_2CH_2-An-CH_2Cl \rightarrow An-CH_2CH_2CH_2-An-CH_2OH$$

$$An-CH_2CH_2CH_2-An-CH_2OH \rightarrow An-CH_2CH_2CH_2-An-COOH$$

The compounds wherein in the linkage is diester or $OOC-CH_2-COO$ are prepared by chloromethylation of the corresponding diester, conversion of the chloromethyl group to the hydroxymethyl group and oxidation of the hydroxymethyl group to a carboxylic acid, as described above. Diester starting materials can be prepared as described in U.S. Pat. Nos. 3,807,999 and 3,892,642.

Alternately, the compounds of the present invention can be prepared by the chloromethylation of the corresponding flexible chain-linked dianthracene compounds $An-R_1-An$, conversion of the chloromethyl group to an aldehyde using the Sommelet reaction (reaction with hexamethylenetetramine followed by mild hydrolysis of the quaternary ammonium salt intermediate). The resultant aldehyde may be utilized as such, reduced to yield the corresponding hydroxymethyl compound or oxidized to yield the corresponding carboxylic acid. The carboxylic acid prepared by this approach, or as described above, can be converted to the corresponding acid chloride by reaction with thionyl chloride, phosphorus trichloride, or the like. The acid chloride can be converted via the azide to the corresponding isocyanate (Curtius degradation).

The polymer-reactive photosensitive anthracene compounds of the present invention are chemically incorporated in polymers, depending on the functional groups already present, or which can be introduced into those polymers. For example, polystyrene can be chloromethylated and photosensitive anthracenes having a hydroxymethyl group will be reactive with the chloromethyl group in the polystyrene. Anthracenes having a chloromethyl group will be reactive with polymers, such as polyvinyl alcohol, which are characterized by the presence of hydroxyl groups. Anthracenes having chloromethyl group will also be reactive with polymers of acrylic and methacrylic acid. Anthracenes having a hydroxymethyl group or a carboxylic acid group will be reactive, respectively, with polyesters having unreactive carboxylic acid or hydroxyl groups present. Anthracenes having a hydroxymethyl group will be reactive with polyurethanes having reactive isocyanate groups present. Conversely, anthracene compounds having an isocyanate group will react with polymers having a hydroxyl group present. Anthracene acid chlorides will react in a similar fashion to those compounds having a carboxylic acid group, but more rapidly and more completely. Anthracene compound having an aldehyde group can react with polymers having amino group. Other combinations of suitable polymer-reactive photosensitive anthracenes and polymers with which they can react will be apparent to those skilled in the art.

Our invention is further illustrated by means of the following non-limiting examples.

EXAMPLE 1

2.38 g (10 mmoles) of $HOCH_2$—An—$CH_2OH$ was dissolved in 250 cc of dimethyl sulfoxide (DMSO) at room temperature and a solution of 0.12 g of sodium hydride (NaH) (5 mmoles) in 35 cc of DMSO added dropwise. After the addition was complete, the reaction mixture was stirred for an additional hour at room temperature. A solution of 2.265 g (10 mmoles) of An—$CH_2Cl$ in DMSO was then added dropwise to the reaction mixture. After another hour of stirring, the product was separated by adding water. Pure An—$CH_2OCH_2$—An—$CH_2OH$ was obtained by gel filtration of the crude product.

EXAMPLE 2

2.08 g (10 mmoles) of An—$CH_2OH$ was dissolved in 200 cc of dimethyl formamide (DMF) at room temperature and a solution of 0.24 g of NaH (10 mmoles) in 40 cc of DMF was added dropwise. After the addition was complete, the mixture was stirred for an additional hour at room temperature. A solution of 2.75 g (10 mmoles) of $ClCH_2$—An—$CH_2Cl$ in DMF (200 cc) was then added dropwise to the reaction mixture over the period of an hour. The product, An—$CH_2OCH_2$—An—$CH_2Cl$, was separated and purified by column chromatography.

EXAMPLE 3

An—$CH_2OCH_2$An—COOH was prepared by the same general procedure as described in Example 1, using An—$CH_2OH$ in place of An—$CH_2Cl$ and $ClCH_2$—An—COOH in place of $HOCH_2$—An—$CH_2OH$.

EXAMPLE 4

Chloromethylated polystyrene was prepared according to the procedure of Feinberg and Merrifield, Tetrahedron, 30, 3209 (1974), using dichloromethane and chloromethyl methyl ether as solvents and zinc chloride as the catalyst. The number of chloromethyl groups on a polymer chain can be controlled by varying the amount of catalyst, reaction time and temperature.

Polymethylphenylsiloxane and copolymers of styrene and can be chloromethylated using the same general procedure.

EXAMPLE 5

Optical recording materials containing intramolecular photodimerizable anthracene from partially chloromethylated polystyrene were prepared as follows: 80 mg ($1.87 \times 10^{-4}$ moles) of An—$CH_2OCH_2$—An—$CH_2OH$ was dissolved in 50 cc of DMF and a solution of 4.5 mg of NaH in 10 cc of DMF was added dropwise to the former. The mixture was stirred for an hour. A solution of 5.61 g of partially chloromethylated polystyrene ($M_{av}=37,400$) in 100 cc of DMF was added dropwise and the reaction mixture stirred for several hours. The polymer was separated by adding water to the mixture and purified by precipitation from methanol.

The purified polymer displayed the characteristic absorption band of anthracene and was very sensitive to U.V. light. In dilute solution, after 15 min. of irradiation at 365 nm with a 200 W Hg lamp, 90% of the anthracene chromophore was dimerized, accompanied by a large change in absorption spectra. In the absence of a solvent, after 15 minutes of irradiation at 45° C., at 365 nm with a 200 W HG lamp, 50% of the anthracene chromophore attached to polystyrene in the purifid polymer was dimerized.

Using a similar procedure, An—$CH_2OCH_2$An—$CH_2OH$ can be reacted into chloromethylated polymethylphenylsiloxane and into chloromethylated polystyrene copolymers.

EXAMPLE 6

To a solution of 2.5 g of polyacrylic acid potassium salt ($M_{av}=250,000$) in 100 cc of DMF, was added a solution of 0.3 g ($6.7 \times 10^{-4}$ moles) of An—$CH_2OCH_2$An—$CH_2Cl$ in 50 cc of DMF. The mixture was stirred at 60° C. overnight. After the reaction was complete, photosensitive polyacrylic acid was precipitated with hexane.

Photosensitive polyoxyethylene and polyvinyl alcohol can be prepared by the same general procedure.

What is claimed is:

1. Compounds of the formula:

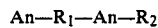

wherein —An represents 9-anthyl, —An— represents 9,10-anthrylidine, $R_1$ is $CH_2$—O—$CH_2$, $CH_2CH_2CH_2$ or OOC—$CH_2$—COO, and $R_2$ is $CH_2Cl$, $CH_2OH$, CHO, COOH, COCL or NCO.

2. A compound according to claim 1, wherein $R_1$ is $CH_2OCH_2$ and $R_2$ is $CH_2OH$.

3. A compound according to claim 1, wherein $R_1$ is $CH_2OCH_2$ and $R_2$ is $CH_2Cl$.

4. A compound according to claim 1, wherein $R_1$ is $CH_2OCH_2$ and $R_2$ is COOH.

* * * * *